US010652520B2

(12) United States Patent
Otto et al.

(10) Patent No.: US 10,652,520 B2
(45) Date of Patent: May 12, 2020

(54) THREE DIMENSIONAL IMAGE CAPTURE

(71) Applicant: Canfield Scientific, Incorporated, Parsippany, NJ (US)

(72) Inventors: Gerhardt Paul Otto, Boonton Township, NJ (US); Athula Mandanayake, Kinnelon, NJ (US)

(73) Assignee: Canfield Scientific, Incorporated, Parisppany, NJ (US)

( * ) Notice: Subject to any disclaimer, the term of this patent is extended or adjusted under 35 U.S.C. 154(b) by 41 days.

(21) Appl. No.: 15/908,169

(22) Filed: Feb. 28, 2018

(65) Prior Publication Data

US 2018/0255292 A1    Sep. 6, 2018

Related U.S. Application Data

(60) Provisional application No. 62/465,560, filed on Mar. 1, 2017.

(51) Int. Cl.
| | | |
|---|---|---|
| *H04N 13/243* | (2018.01) | |
| *G06T 7/521* | (2017.01) | |
| *H04N 13/254* | (2018.01) | |
| *H04N 13/25* | (2018.01) | |
| *A61B 5/00* | (2006.01) | |
| *A45D 44/00* | (2006.01) | |

(52) U.S. Cl.
CPC ......... *H04N 13/243* (2018.05); *A61B 5/0064* (2013.01); *A61B 5/444* (2013.01); *G06T 7/521* (2017.01); *H04N 13/25* (2018.05); *H04N 13/254* (2018.05); *A45D 2044/007* (2013.01)

(58) Field of Classification Search
None
See application file for complete search history.

(56) References Cited

U.S. PATENT DOCUMENTS

| | | | |
|---|---|---|---|
| 2011/0102550 A1 | 5/2011 | Daniel et al. | |
| 2014/0243685 A1 | 8/2014 | Patwardhan et al. | |
| 2014/0341484 A1* | 11/2014 | Sebring | G06T 15/205 |
| | | | 382/284 |
| 2015/0119652 A1 | 4/2015 | Hyde et al. | |
| 2015/0196109 A1* | 7/2015 | Edgar | A61B 5/442 |
| | | | 132/320 |
| 2016/0275681 A1* | 9/2016 | D'Alessandro | G06T 3/4038 |
| 2016/0314585 A1* | 10/2016 | Thomas | G06T 7/0012 |

OTHER PUBLICATIONS

International Search Report and Written Opinion of the International Searching Authority, PCT/US2018/020261, dated May 9, 2018.
Chieh-han John Tzou et al, "Comparison of three-dimensional surface-imaging systems," Journal of Plastic, Reconstructive & Aesthetic Surgery, Apr. 1, 2014.
Indermeet Kohli et al, "Three-dimensional imaging of vitiligo," Experimental Dermatology, vol. 24, Jun. 3, 2015, pp. 379-880.
(Continued)

*Primary Examiner* — Sath V Perungavoor
*Assistant Examiner* — Tyler B Edwards

(57) ABSTRACT

Apparatuses and methods are disclosed for capturing three-dimensional images, particularly of all or parts of human subjects and employing polarization. In disclosed implementations, cross-polarized, whole-body images of human subjects can be captured.

20 Claims, 7 Drawing Sheets

(56) References Cited

OTHER PUBLICATIONS

Dr. Allan Halpern et al, "Dr. Allan Halpern 3-D images aid total body mole mapping," Dermatology News, Oct. 2, 2014.
Michael Landsberg, "Landsberg: Canfield: First class in medical and aesthetic imaging," Jan. 1, 2017.
Dermatology Times, "Facial imaging system detects subsurface vascular conditions," Apr. 1, 2008.
www.Canfieldsci.com, "Visia complexion analysis," Jun. 1, 2016.

* cited by examiner

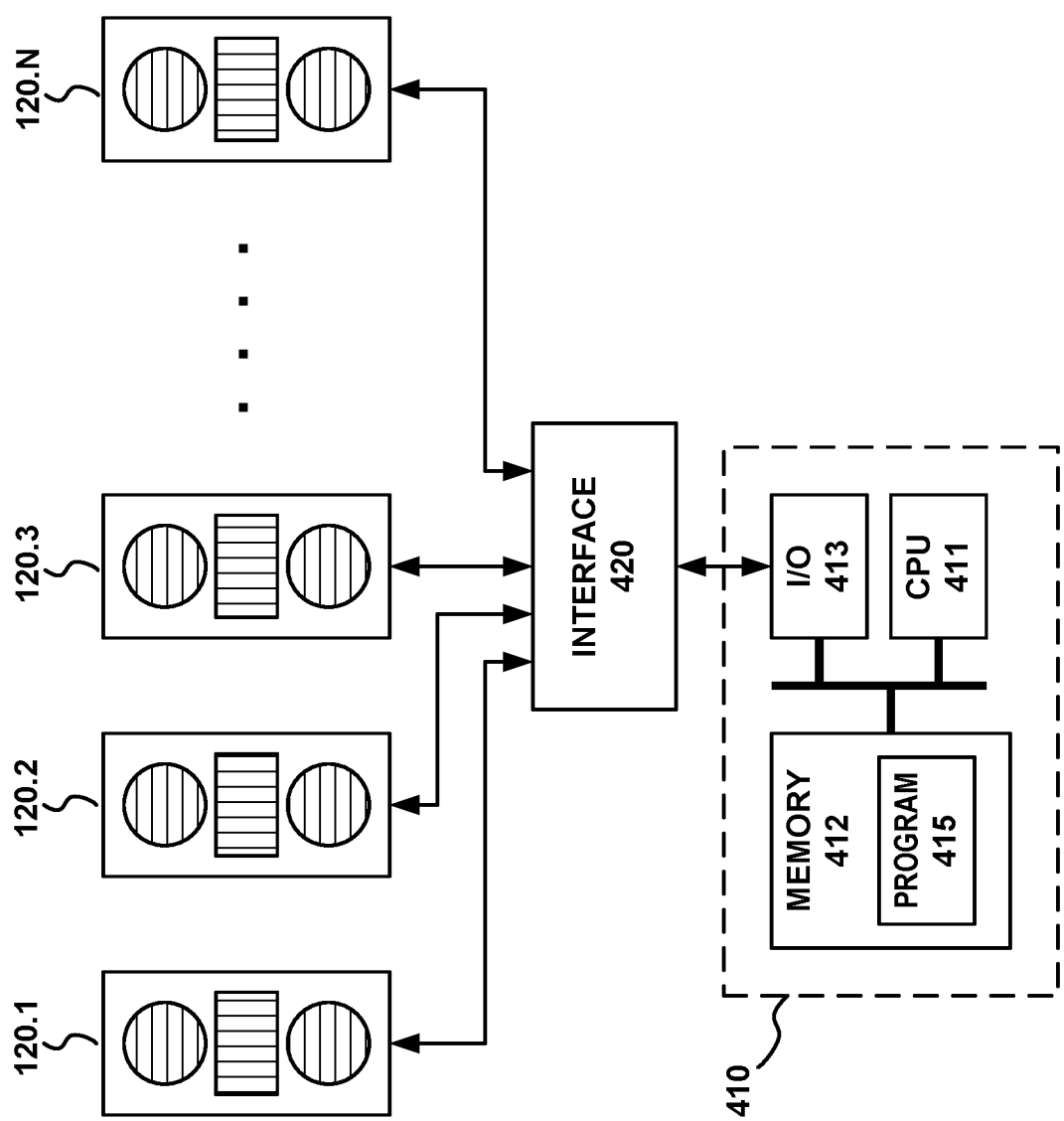

THREE DIMENSIONAL IMAGE CAPTURE

RELATED APPLICATIONS

This Application claims priority from U.S. Provisional Patent Application No. 62/465,560, filed Mar. 1, 2017 and incorporated herein by reference in its entirety.

BACKGROUND INFORMATION

The present disclosure relates to three-dimensional image capture, particularly with the use of polarized light.

The capture of three-dimensional (3D) images of a subject, such as a human, typically entails the use of multiple cameras and light sources, arranged about the subject, that are activated simultaneously while the subject remains still. The number of cameras and light sources required depends in direct relation on the size of the area to be imaged. An example of an imaging system for imaging a whole body is the VECTRA® WB360 from Canfield Scientific, Inc. which employs 92 DSLR cameras and 14 white-light sources.

For some applications, imaging modalities other than reflectance white-light images are needed. As an example, for imaging sub-surface features of tissue such as human skin, cross-polarized imaging can be used to reduce or eliminate surface reflections. In such a modality, an area of interest is illuminated with light of a first polarization and captured through filtering of a different, typically orthogonal polarization. The area of interest, however, that can be effectively imaged with such a modality is typically small, such as a region or patch of skin representing a relatively small portion of a whole body.

While existing systems such as the above-mentioned are capable of capturing high quality whole-body white-light images, the capture of high quality, whole-body cross-polarization images has heretofore been problematic.

SUMMARY OF THE DISCLOSURE

In a first aspect, the present disclosure sets out an apparatus comprising: a plurality of image capture devices, each including polarized filtering of a first orientation; a plurality of illumination sources, each including polarized filtering of a second orientation orthogonal to the first orientation; a support structure, wherein the plurality of image capture devices and the plurality of illumination sources are mounted on the support structure; and a controller, wherein the controller is configured to control the plurality of image capture devices and the plurality of illumination sources to sequentially activate groups of the plurality of image capture devices and to sequentially activate groups of the plurality of illumination sources, wherein each group of illumination sources is activated while a respective group of image capture devices is activated.

In a second aspect, the first orientation is horizontal and the second orientation is vertical.

In a third aspect, only one group of illumination sources is activated at a time.

In a fourth aspect, a first of the groups of image capture devices and a first of the groups of illumination devices are mounted on a left portion of the support structure and a second of the groups of image capture devices and a second of the groups of illumination devices are mounted on a right portion of the support structure.

In a fifth aspect, the plurality of image capture devices and the plurality of illumination sources are arranged in a plurality of imaging modules, each imaging module including at least one image capture device and at least one illumination source and said at least one illumination source is activated while said at least one image capture device is activated.

In a sixth aspect, the at least one image capture device and the at least one illumination source are arranged along an axis of the module that lies in a vertical plane that is to intersect a subject to be imaged.

In a seventh aspect, the apparatus comprises a plurality of unpolarized illumination sources, wherein the plurality of unpolarized illumination sources are mounted on the support structure and wherein the controller is configured to control the plurality of unpolarized illumination sources.

In an eighth aspect, the plurality of image capture devices are oriented so that the optical axis of each image capture device is normal to an area of a subject to be imaged.

In a ninth aspect, the plurality of image capture devices and the plurality of illumination sources are arranged to image at least one side of a human body.

In a tenth aspect, the present disclosure sets out a system comprising first and second apparatuses as set out above.

In an eleventh aspect, the present disclosure sets out a method of operation of a three-dimensional imaging apparatus comprising a plurality of image capture devices, each including polarized filtering of a first orientation, and a plurality of illumination sources, each including polarized filtering of a second orientation orthogonal to the first orientation, the method comprising: sequentially activating groups of the plurality of image capture devices; and sequentially activating groups of the plurality of illumination sources, wherein each group of illumination sources is activated while a respective group of image capture devices is activated.

In an twelfth aspect, only one group of illumination sources is activated at a time in the method as set out above.

In a thirteenth aspect, the present disclosure sets out a non-transient computer readable storage medium containing instructions for execution by a processor for carrying out the method as set out above.

In a fourteenth aspect, the present disclosure sets out a cross-polarization imaging apparatus comprising: an image capture device, the image capture device including polarized filtering of a first orientation; an illumination source, the illumination source including polarized filtering of a second orientation orthogonal to the first orientation; a housing configured to house the image capture device and the illumination source; and circuitry configured to interoperate with the image capture device, the illumination source and a controller, so that the controller can control the image capture device and the illumination source.

In a fifteenth aspect, the first orientation is horizontal, and the image capture device and the illumination source are arranged along or parallel to a vertical axis of the module.

In a sixteenth aspect, the cross-polarization imaging apparatus comprises a further image capture device, the further image capture device including polarized filtering of the first orientation, wherein the illumination source is arranged between the image capture devices.

In a seventh aspect, the first orientation is horizontal and the second orientation is vertical in the cross-polarization imaging apparatus.

These and other aspect are shown and described below in greater detail.

BRIEF DESCRIPTION OF THE DRAWINGS

FIG. 4 is a schematic representation of an exemplary system in accordance with the present disclosure.

DETAILED DESCRIPTION

Figure 1:
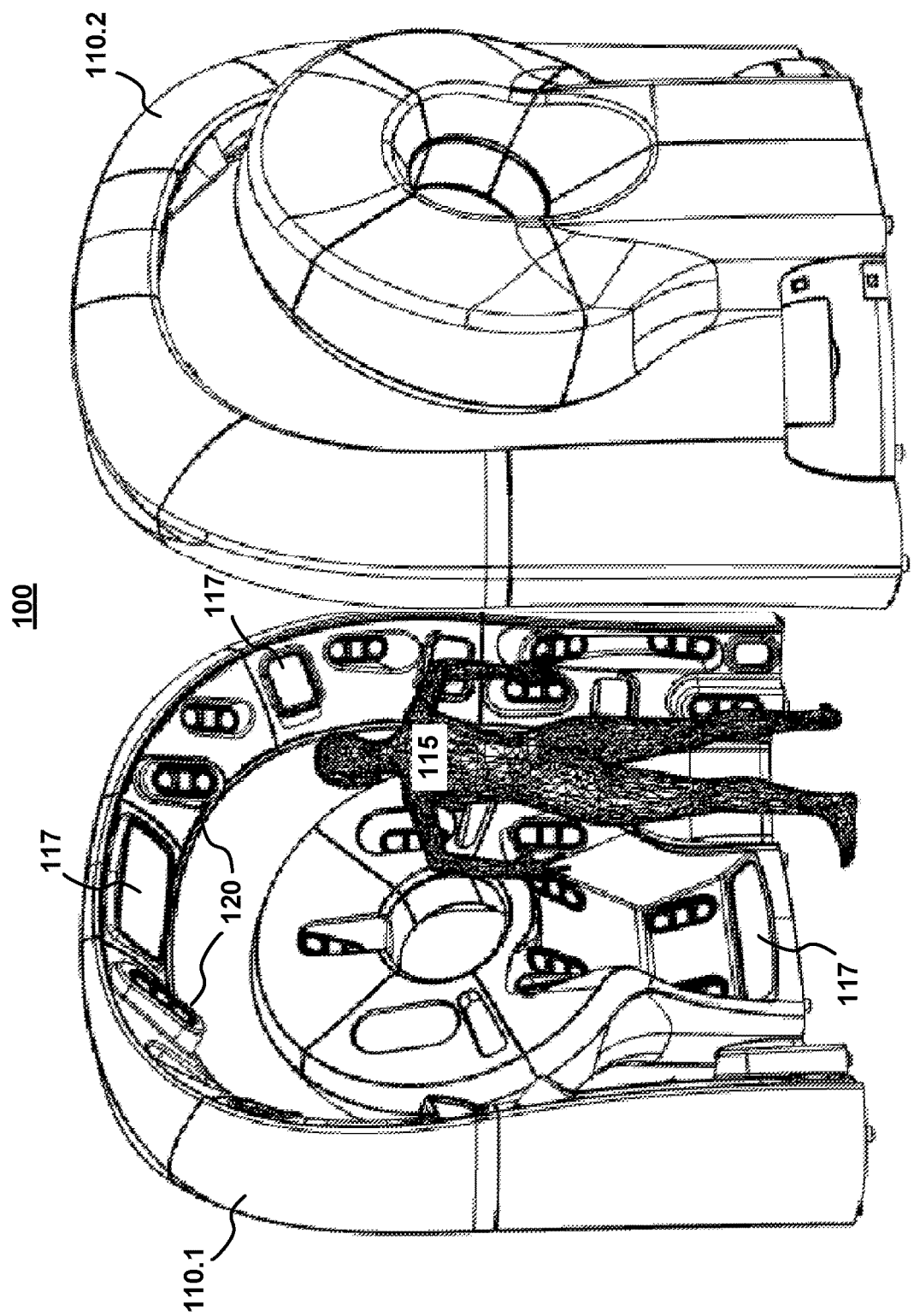
FIG. 1 is a perspective view of a whole-body imaging system as may be used in embodiments of the present disclosure.

FIG. 1 is a perspective view of a whole-body imaging system 100 as may be used in embodiments of the present disclosure. System 100 comprises two units 110, each unit operable to image the front and back sides of a subject 115 when situated therebetween. In exemplary embodiments, the units 110 can operate individually, in a standalone configuration, or in conjunction with each other, as shown in FIG. 1.

Each unit 110 comprises multiple modules 120, each comprising one or more image capture devices (e.g., DSLR cameras) and one or more light sources. As described in greater detail below with reference to FIG. 2, in exemplary embodiments, each module 120 includes a light source of a first polarization and two cameras with polarized filtering orthogonal to that of the light source, thereby enabling cross-polarized imaging. Additional light sources 117 may be included to provide unpolarized white-light illumination for conventional imaging. Additional light sources 117 and modules 120 are mounted on a support structure, with positions and orientations suitable for illuminating and capturing images of the subject 115.

In exemplary embodiments, the units 110 can be identical and/or can be configured, such as by adjustment of the orientation of one or more modules 120, so as to optimize the imaging of features on the respective sides of the subject 115.

Figure 2:
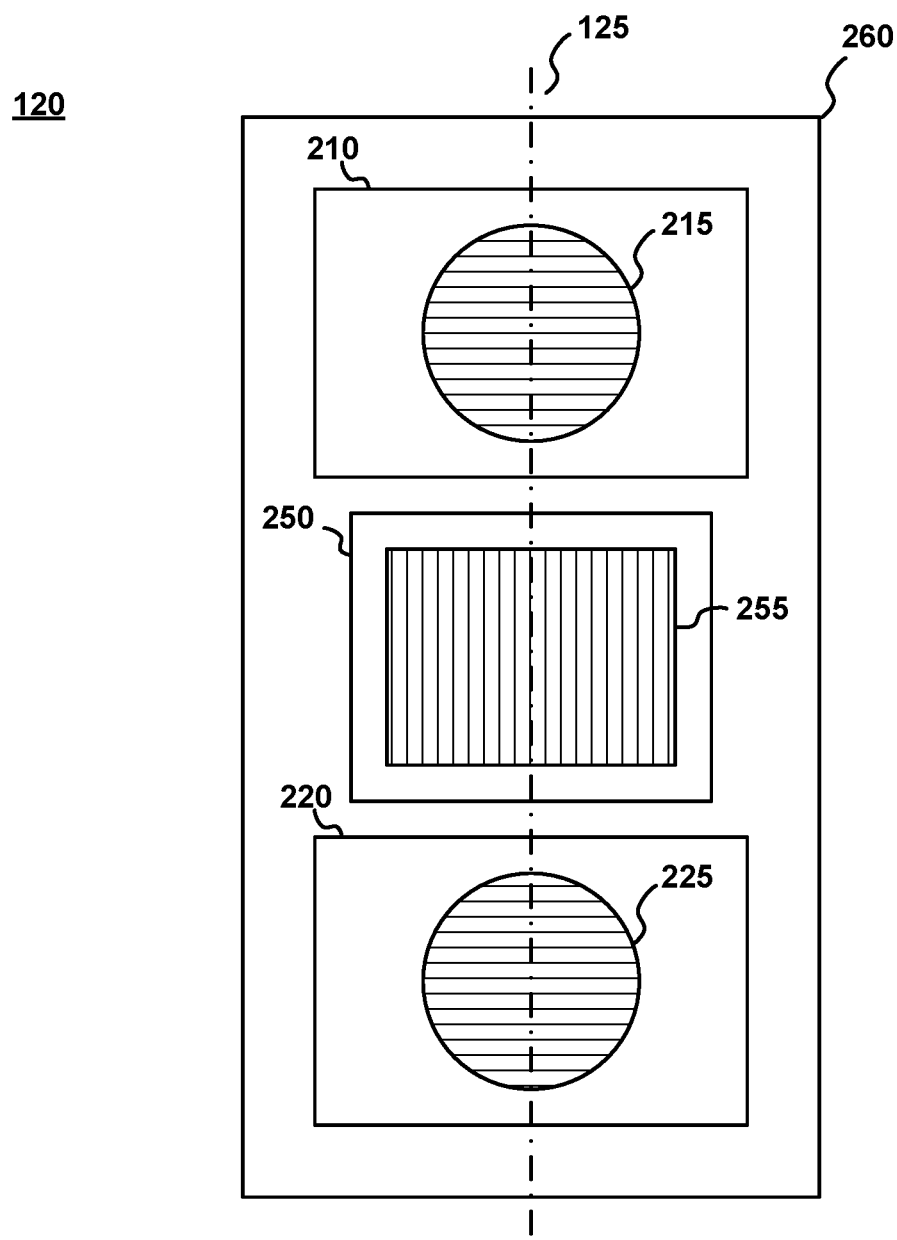
FIG. 2 is a schematic depiction of an exemplary embodiment of an imaging module as may be used in a whole-body imaging system such as that of FIG. 1.

FIG. 2 schematically shows an exemplary embodiment of a module 120 comprising an arrangement of a first camera 210, a second camera 220 and a light source 250 arranged between the two cameras. Cameras 210, 220 and light source 250 are arranged in a housing 260, which can be mounted in unit 110. Cameras 210 and 220 are configured with horizontally oriented linear polarizers 215 and 225, respectively, so that light captured thereby is horizontally polarized. Light source 250 is configured with a vertically oriented linear polarizer 255, so that light emitted thereby is vertically polarized. As shown in the exemplary embodiment of FIG. 2, cameras 210, 220 and light source 250 are aligned generally along or parallel to a vertical axis 125 of the module.

In exemplary embodiments, each camera 210, 220 can be implemented with a conventional DSLR camera, such as, for example, a Canon T6 DSLR. Light source 250 can be implemented with one or more xenon flash bulbs, although other illumination sources can be used, such as LEDs, depending on the desired characteristics. Considerations in the selection of light source 250 may include, for example, illumination intensity, spectral distribution, response time, power consumption, and size, among others.

Figure 3:
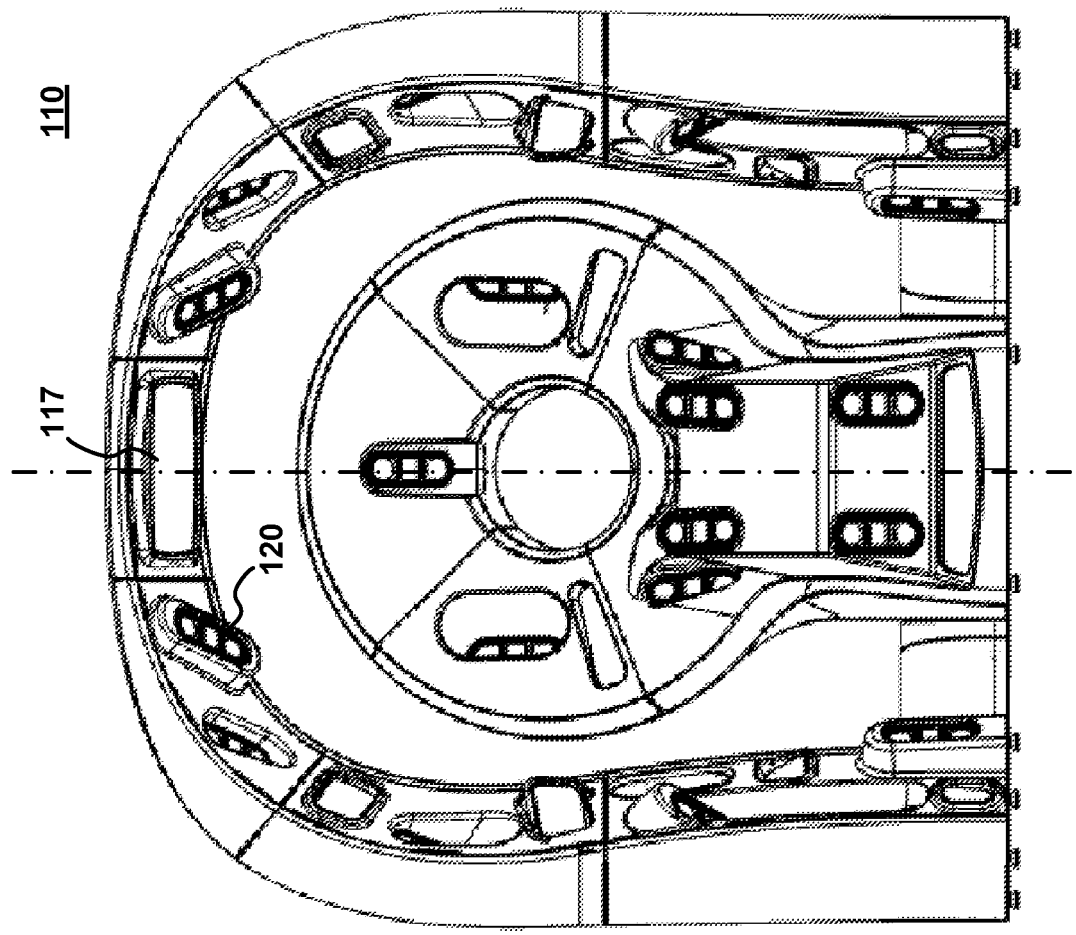
FIG. 3 is an elevation view of an imaging apparatus as may be used in the system of FIG. 1.

FIG. 3 is an elevation view of a unit 110. Modules 120 and light sources 117 are preferably arranged symmetrically about a center line of unit 110. Additionally, each module 120 is oriented so that its axis 125 lies in a plane that is vertical and that intersects the subject 115. The modules 120 are oriented to point at various portions of the subject 115. More specifically, modules 120 are preferably oriented so that the optical axis of each camera is normal or as normal as practicable (hereinafter "normal"), to the area on the subject 115 at which it is pointed. Similarly, light emitted from the light sources is incident preferably normally, or within 45 degrees of normal, to the area of the subject 115 being imaged.

With this arrangement of modules 120, it is contemplated that an entire side of the subject can be imaged. As can be appreciated, for imaging smaller portions of the subject, a subset of the modules 120 shown can be used, accordingly. In an exemplary embodiment, each unit 110 includes 46 cameras and 23 cross-polarized light sources arranged in 23 modules 120.

FIG. 4 is a block diagram schematically depicting an exemplary arrangement of modules 120, a computer 410 and an interface 420, therebetween. In exemplary embodiments, it is contemplated that computer 410 can be implemented with a personal computer or the like and includes elements typical of such devices, such as a central processing unit (CPU) 411, memory 412 (e.g., RAM, ROM, EEPROM, flash, diskdrive, SD card, etc.), and input/output (I/O) 413 (e.g., keyboard, display, communications, etc.) As is typical of computing devices, CPU 411 executes software stored in memory 412 so as to cause computer 410 to operate, as manifested via I/O 413, in accordance with the software. While CPU 411 will typically execute a wide array of software to perform various functions, the software of interest for purposes of the present description includes image capture program 415, which when executed causes system 100 to operate as described in greater detail below.

In exemplary embodiments, each module 120 includes circuitry allowing interaction between the cameras and light source therein and computer 410 via interface 420.

Modules 120 and computer 410 intercommunicate via interface 420, which may include wired and/or wireless, analog and/or digital, and standardized and/or proprietary elements, including but not limited to Universal Serial Bus (USB), Ethernet, radio frequency (RF) communications (e.g., Near Field Communications (NFC), Wifi, Bluetooth), inductive, infrared, or acoustic, among others. In operation, interface 420 is used to convey signals to modules 120 relating to image capture operations using the cameras and light sources of the modules 120. Responsive to such signals, the cameras and light sources of the modules 120 operate to capture multiple cross-polarized images of the subject 115, as described below in greater detail with reference to FIGS. 5-7.

Interface 420 can also be used to pass a variety of information between computer 410 and modules 120, including but not limited to status and/or configuration information.

The operation of the exemplary system of FIGS. 1-4 will now be described with reference to FIGS. 5-7.

Figure 5A:
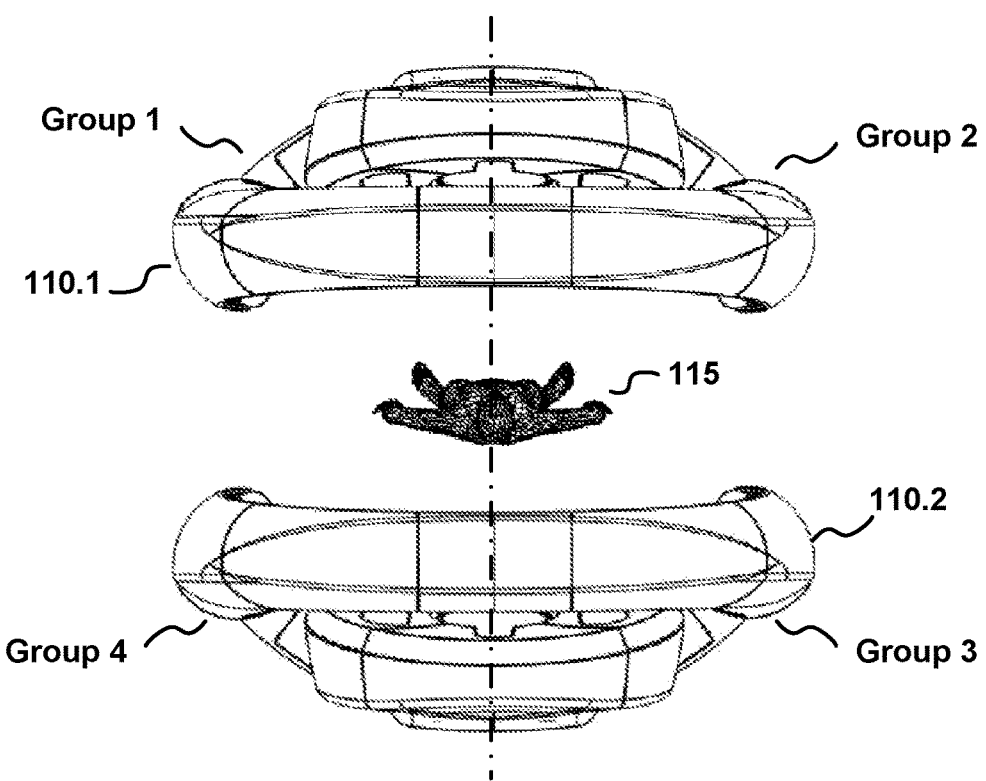
FIGS. 5A and 5B show the grouping of image capture devices and illumination sources in a whole-body imaging system such as that of FIG. 1.
Figure 5B:
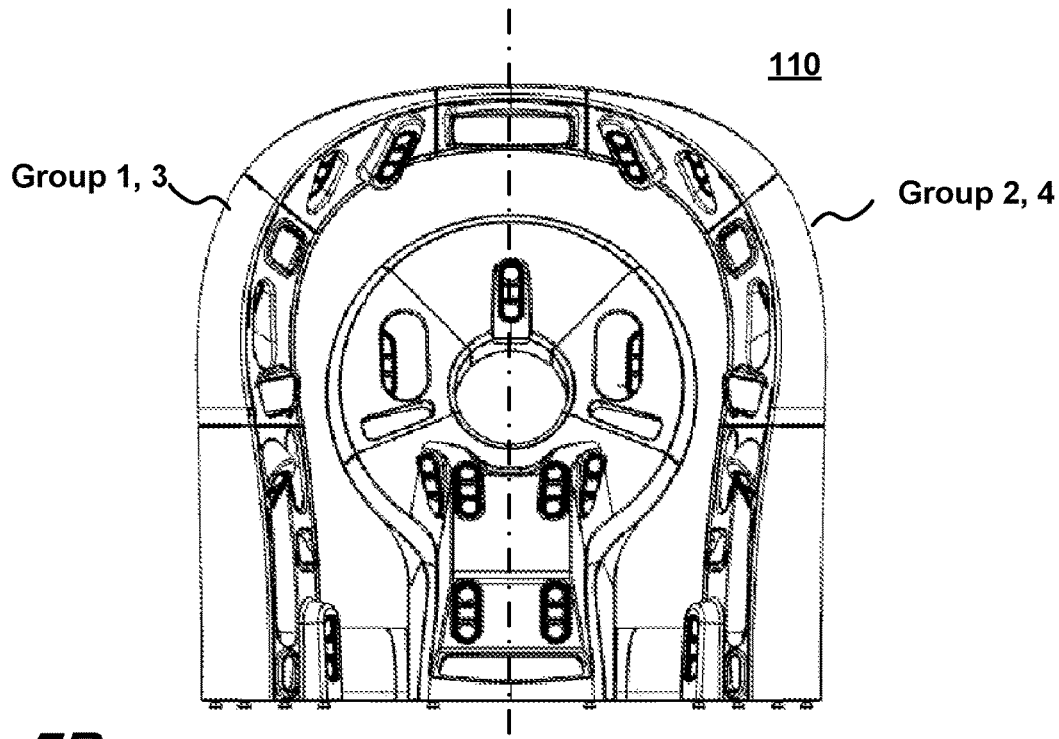

In exemplary embodiments, it is contemplated that computer 410 can concurrently interact with all or selected subsets of the modules 120 of system 100. In an exemplary embodiment, computer 410 concurrently controls subsets, or groups, of modules 120 selected as illustrated in FIGS. 5A and 5B. For instance, the modules 120 to the left of the centerline of unit 110 are assigned to a first group, whereas those to the right are assigned to a different group. (A module on the centerline is assigned to one group or the other. In other embodiments, there can be an odd number of groups for each unit 110, such as for example, a left, center, and right group.) Computer 410 controls the modules of each group so that the shutters of the cameras of those modules open and close together and so that the light sources of those modules flash together, within some relatively small timing differential, such as may be due to variations between the cameras and light sources in the group of modules. As shown in FIGS. 5A and 5B, the modules 120 of exemplary system 100 are organized into four groups 1-4, two for each unit 110. Other numbers of groups (two or greater) may also be used in various embodiments consistent with the present disclosure.

Figure 6:
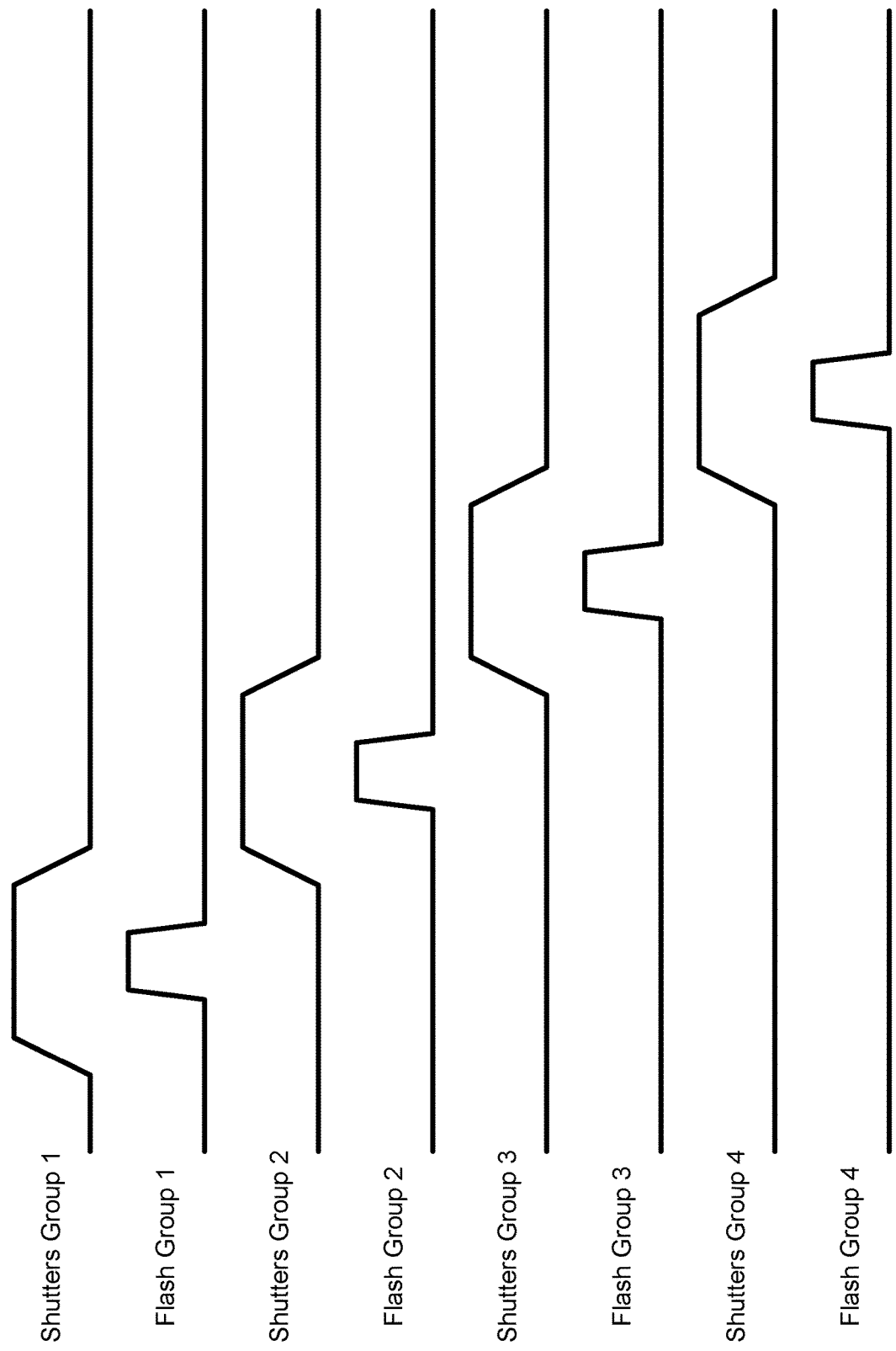
FIG. 6 is a timing diagram schematically illustrating an exemplary sequence of events occurring in the operation of the system of FIGS. 1-5 to capture a whole-body cross-polarized image.

FIG. 6 is a timing diagram schematically illustrating an exemplary sequence of events occurring in the operation of the exemplary system of FIGS. 1-5 to capture a whole-body cross-polarized image. As shown in FIG. 6, the shutters of the cameras in the modules of group 1 are first opened. While the shutters of the group 1 cameras are open, the light sources of group 1 are flashed. The shutters of the group 1 cameras are then closed. The same sequence of events is followed successively for groups 2-4. It should be noted that while there may be some or no overlap in the opened states of shutters of successively activated groups, when the light sources of a given group of modules are flashed, preferably only the shutters of that group are open. Additionally, the groups of modules can be activated in any order (e.g., 4-3-2-1, 1-3-2-4, 4-2-3-1, 1-4-2-3, etc.)

By sequentially activating the groups of modules, the cameras of a group capture images of those areas of the subject 115 that are illuminated only by light sources of that group. As such, the cameras of each group capture only light reflected from the light sources of the same group and do not capture light from the light sources of any other group, either directly or reflected from the subject.

Figure 7:
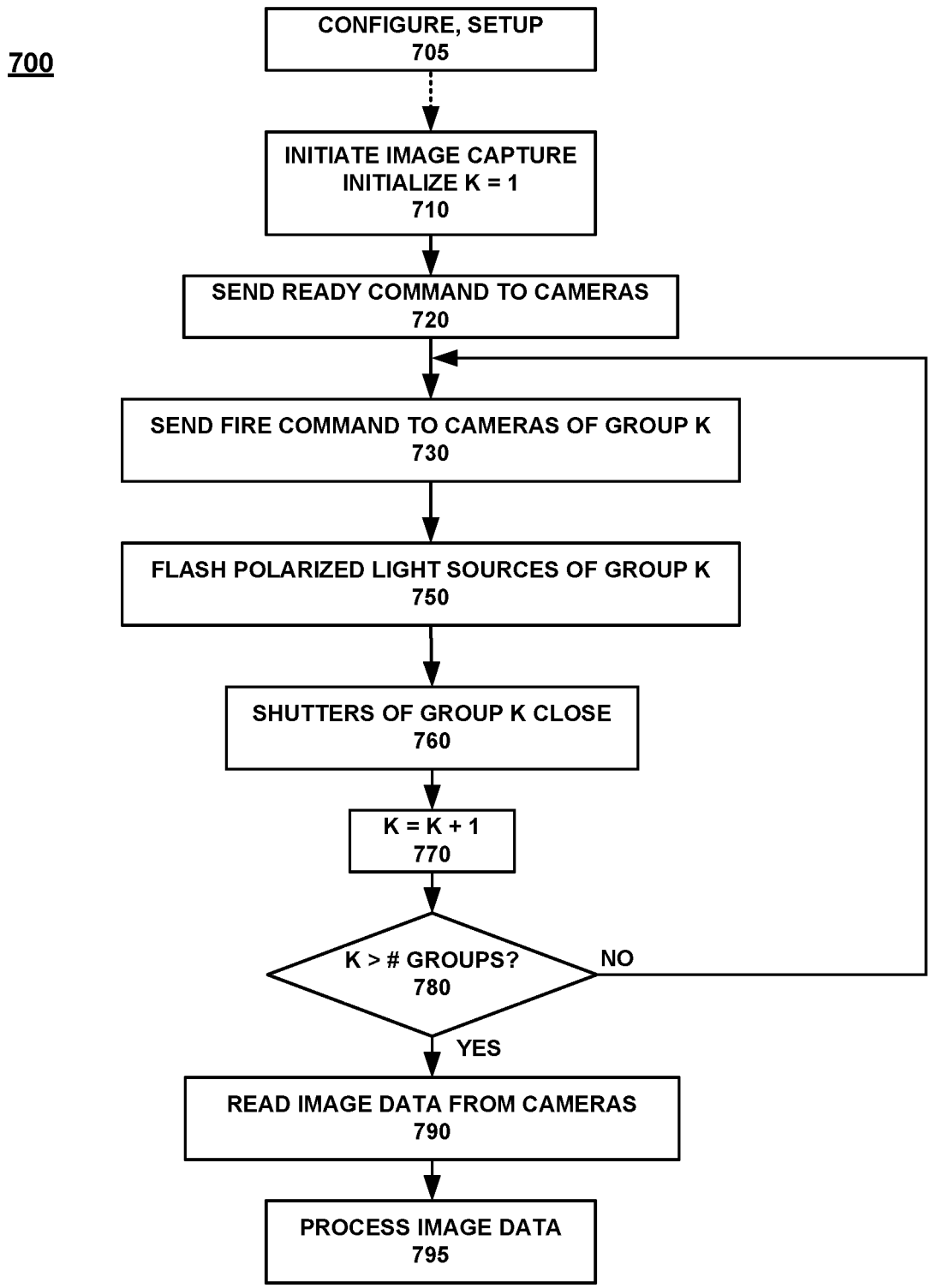
FIG. 7 is a flowchart depicting an exemplary image capture process in accordance with the present disclosure.

FIG. 7 is a flowchart depicting an exemplary image capture process 700, such as would be carried out with exemplary imaging system 100 in accordance with the present disclosure. It is contemplated that in carrying out the exemplary image capture process, the system 100 operates in accordance with program 415 stored in memory 412 and executed by CPU 411.

As shown in FIG. 7, operation begins at 705 with the configuration of the system 100. In exemplary embodiments, the cameras of system 100 are configured in a manual capture mode, with fixed focus, and with appropriate ISO and shutter speed settings. Additionally, circuitry for controlling the light sources of modules 120 may also be configured as needed, such as by loading values of parameters for controlling the light sources, including, for example, timing and/or brightness settings.

At some point 710 after configuration of the system, the capture of a cross-polarized image is initiated. This includes initializing a counter K representing one of a plurality of groups of modules 120 to be activated. In this example, the number of module groups is four and counter K is initialized to one.

Operation then continues to 720 in which a "ready" command is sent to all of the cameras of the system 100. This command instructs the cameras to prepare to capture an image, similar to a partial press of the shutter button on a typical DSLR camera.

After a delay, at 730 a "fire" command is sent to all of the cameras of group K, starting with group 1, as shown in FIGS. 5A and 5B. The fire command is similar to a full depression of the shutter button on a typical DSLR camera.

Operation then proceeds to 750 in which the polarized light sources of group K are flashed concurrently. In exemplary embodiments, circuitry in each of the modules 120 turns the respective light source 250 on and off in response to one or more commands from computer 410. The computer 410 can provide one command to flash the light sources and the circuitry of each module 120 can determine when to turn its respective light source on and off based on one or more timing parameters, which may be set upon configuration at 705. In alternative embodiments, computer 410 can provide a first command to turn the light sources on and a second command to turn the light sources off. In any case, the flashing of the light sources of group K may be delayed after the fire command is sent at 730 so as to provide sufficient time for the shutters of the cameras of group K to be fully open when the light sources of group K are flashed.

After completion of the flash, the shutters of the cameras of group K are closed at 760. In an exemplary embodiment, the shutters are closed an interval of time after they are opened, which is set during configuration of the cameras at 705. Alternatively, the shutters can be closed responsive to a further command from computer 410.

At 770, the group counter K is incremented and at 780 a determination is made as to whether all of the groups of modules have been activated, such as by determining whether the counter K, as incremented at 770, exceeds the number of module groups. If not, operation loops back to 730 and the above-described operation is repeated for the next group of modules in the sequence.

Once it is determined at 780 that all groups of modules have been activated, operation proceeds to 790 in which computer 410 interacts with the cameras to obtain the images captured thereby during the above-described image capture procedure. Once computer 410 has obtained the captured images from all of the cameras, operation proceeds to 795 in which the images are processed. Processing of the images may include, for example, adjusting one or more parameters thereof (e.g., dimensions, brightness, hue, gamma, etc.), stitching the images together, generating a three-dimensional model, analyzing, compressing, storing, and transmitting, among other possibilities.

In some embodiments, after sending the fire command at 730 and before the flashing of light sources of group K at 750, operation can optionally include waiting to receive confirmation that the shutters of all of the cameras in group K are in an open state. In such embodiments, this can be done, for example, by monitoring the hotshoes of the cameras in group K, such as with circuitry in the modules 120 which is coupled to the hotshoes and is in communication with computer 410.

The foregoing merely illustrates principles of the invention and it will thus be appreciated that those skilled in the art will be able to devise numerous alternative arrangements which, although not explicitly described herein, embody the principles of the invention and are within its spirit and scope. For instance, as can be appreciated, a variety of arrangements of cameras and light sources are contemplated consistent with the present disclosure, including arrangements in which cameras and light sources are not arranged in modules, or are arranged in modules with different numbers of cameras and light sources, or with different arrangements of camera(s) and light source(s). Moreover, while one or more embodiments have been described in which cameras are configured with horizontally oriented linear polarizers and light sources with vertically oriented linear polarizers, other orientations are also contemplated by the present disclosure (e.g., cameras with vertically oriented polarizers and light sources with horizontally oriented polarizers, or other mutually orthogonal orientations between horizontal and vertical). In addition, while embodiments using a cross-polarization imaging modality have been described, embodiments in accordance with the present disclosure may also be adapted for other imaging modalities, including, for example parallel-polarization and fluorescence imaging modalities, 2D, 3D or dynamic imaging in reflected light, and imaging of any suitable wavelength. Additionally, although illustrated as single elements, each such block or step shown may be implemented with multiple blocks or steps, or various combinations thereof. Also terms such as "software," "application," "program," "firmware," or the like, are intended to refer, without limitation, to any instruction or set of instructions, structure, or logic embodied in any suitable machine-readable medium. It is to be understood that numerous modifications may be made to the illustrative embodiments and that other arrangements may be devised without departing from the spirit and scope of the present invention as defined by the appended claims.

What is claimed is:

1. A three-dimensional imaging apparatus comprising:
   a plurality of image capture devices, each image capture device including polarized filtering of a first orientation and belonging to one of a number of groups of image capture devices;
   a plurality of illumination sources, each illumination source including polarized filtering of a second orientation orthogonal to the first orientation and belonging to one of a number of groups of illumination sources, each of the groups of image capture devices corresponding to one of the groups of illumination sources;
   a support structure, wherein the plurality of image capture devices and the plurality of illumination sources are mounted on the support structure; and
   a controller, wherein the controller is configured to control the plurality of image capture devices and the plurality of illumination sources to sequentially activate each of the groups of image capture devices and each of the groups of illumination sources, wherein each group of illumination sources is activated while the corresponding group of image capture devices is activated.

2. The apparatus of claim 1, wherein the first orientation is horizontal and the second orientation is vertical.

3. The apparatus of claim 1, wherein only one group of illumination sources is activated at a time.

4. The apparatus of claim 1, wherein a first of the groups of image capture devices and a first of the groups of illumination devices are mounted on a left portion of the support structure and a second of the groups of image capture devices and a second of the groups of illumination devices are mounted on a right portion of the support structure.

5. The apparatus of claim 1, wherein the plurality of image capture devices and the plurality of illumination sources are arranged in a plurality of imaging modules, each imaging module including at least one image capture device and at least one illumination source, and wherein said at least one illumination source is activated while said at least one image capture device is activated.

6. The apparatus of claim 5, wherein the at least one image capture device and the at least one illumination source are arranged along an axis of the module that lies in a vertical plane that is to intersect a subject to be imaged.

7. The apparatus of claim 1, comprising a plurality of unpolarized illumination sources, wherein the plurality of unpolarized illumination sources are mounted on the support structure and wherein the controller is configured to control the plurality of unpolarized illumination sources.

8. The apparatus of claim 1, wherein the plurality of image capture devices are oriented so that the optical axis of each image capture device is normal to an area of a subject to be imaged.

9. The apparatus of claim 1, wherein the plurality of image capture devices and the plurality of illumination sources are arranged to image at least one side of a human body.

10. A system comprising first and second apparatuses in accordance with claim 1.

11. The apparatus of claim 1, wherein:
    each group of illumination sources and the corresponding group of image capture devices are mounted on the support structure to point at an area of a subject to be imaged, and
    different corresponding groups of illumination sources and image capture devices are mounted on the support structure to point at different areas of the subject to be imaged.

12. The apparatus of claim 1, wherein the number of groups of image capture devices is the same as the number of groups of illumination sources.

13. A method of operation of a three-dimensional imaging apparatus comprising a plurality of image capture devices, each image capture device including polarized filtering of a first orientation and belonging to one of a number of groups of image capture devices, and a plurality of illumination sources, each illumination source including polarized filtering of a second orientation orthogonal to the first orientation and belonging to one of a number of groups of illumination sources, each of the groups of image capture devices corresponding to one of the groups of illumination sources, the method comprising:
    sequentially activating each of the groups of image capture devices; and
    sequentially activating each of the groups of illumination sources, wherein each group of illumination sources is activated while the corresponding group of image capture devices is activated.

14. The method of claim 13, wherein only one group of illumination sources is activated at a time.

15. A non-transient computer readable storage medium containing instructions for execution by a processor for carrying out the method of claim 13.

16. The method of claim 13, wherein:
    each group of illumination sources and the corresponding group of image capture devices point at an area of a subject to be imaged, and
    different corresponding groups of illumination sources and image capture devices point at different areas of the subject to be imaged.

17. A cross-polarization imaging apparatus comprising:
    an image capture device, the image capture device including polarized filtering of a first orientation;
    an illumination source, the illumination source including polarized filtering of a second orientation orthogonal to the first orientation;
    a housing configured to house the image capture device and the illumination source; and circuitry configured to interoperate with the image capture device, the illumination source and a controller, so that the controller can control the image capture device and the illumination source.

18. The apparatus of claim 17, wherein the image capture device and the illumination source are arranged along or parallel to a vertical axis of the module.

19. The apparatus of claim 18 comprising a further image capture device, the further image capture device including polarized filtering of the first orientation, wherein the illumination source is arranged between the image capture devices.

20. The apparatus of claim 17, wherein the first orientation is horizontal and the second orientation is vertical.

* * * * *